United States Patent
Johnston et al.

(10) Patent No.: US 9,493,789 B2
(45) Date of Patent: Nov. 15, 2016

(54) AUTOMATED GENERATION OF GENETICALLY MODIFIED STEM CELLS

(71) Applicant: Miltenyi Biotec GmbH, Bergisch Gladbach (DE)

(72) Inventors: Ian Johnston, Roesrath (DE); Volker Huppert, Kuerten (DE); Michael Essl, Bergische Gladbach (DE); Stefan Miltenyi, Bergische Gladbach (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 0 days.

(21) Appl. No.: 14/689,105

(22) Filed: Apr. 17, 2015

(65) Prior Publication Data

US 2015/0307900 A1 Oct. 29, 2015

Related U.S. Application Data

(60) Provisional application No. 61/983,534, filed on Apr. 24, 2014.

(51) Int. Cl.

| | |
|---|---|
| *C12N 15/86* | (2006.01) |
| *C12N 15/87* | (2006.01) |
| *C12N 7/00* | (2006.01) |
| *A61K 48/00* | (2006.01) |
| *C12N 5/0783* | (2010.01) |
| *C12N 5/0789* | (2010.01) |
| *C12N 15/64* | (2006.01) |

(52) U.S. Cl.
CPC ........... *C12N 15/86* (2013.01); *A61K 48/0091* (2013.01); *C12N 5/0636* (2013.01); *C12N 5/0647* (2013.01); *C12N 7/00* (2013.01); *C12N 15/64* (2013.01); *C12N 15/87* (2013.01); *C12N 2510/00* (2013.01); *C12N 2740/10051* (2013.01); *C12N 2740/15043* (2013.01)

(58) Field of Classification Search
None
See application file for complete search history.

(56) References Cited

FOREIGN PATENT DOCUMENTS

WO   WO09072003 A2 *  6/2009  ............. A61M 1/36

\* cited by examiner

*Primary Examiner* — Robert M Kelly
(74) *Attorney, Agent, or Firm* — Jaquelin K. Spong

(57) ABSTRACT

The invention relates to a process for generation of genetically modified stem cells comprising the steps
a) providing a cell sample in suspension comprising stem cells in a centrifugation chamber comprising a base plate and cover plate connected by a cylinder
b) adjusting the volumetric concentration of stem cells in the cell sample to at least $1 \times 10^5$ stem cells per mL cell sample by centrifugation
c) introducing viral and/or non-viral vectors to the centrifugation chamber for genetically modifying the stem cells
d) adjusting the spatial concentration of stem cells in the centrifugation chamber by rotating the centrifugation chamber at a speed where the cell sample is located at the outermost 35% of the radius of the base plate of the centrifugation chamber, thereby inducing gene modification of the stem cells.

13 Claims, 8 Drawing Sheets

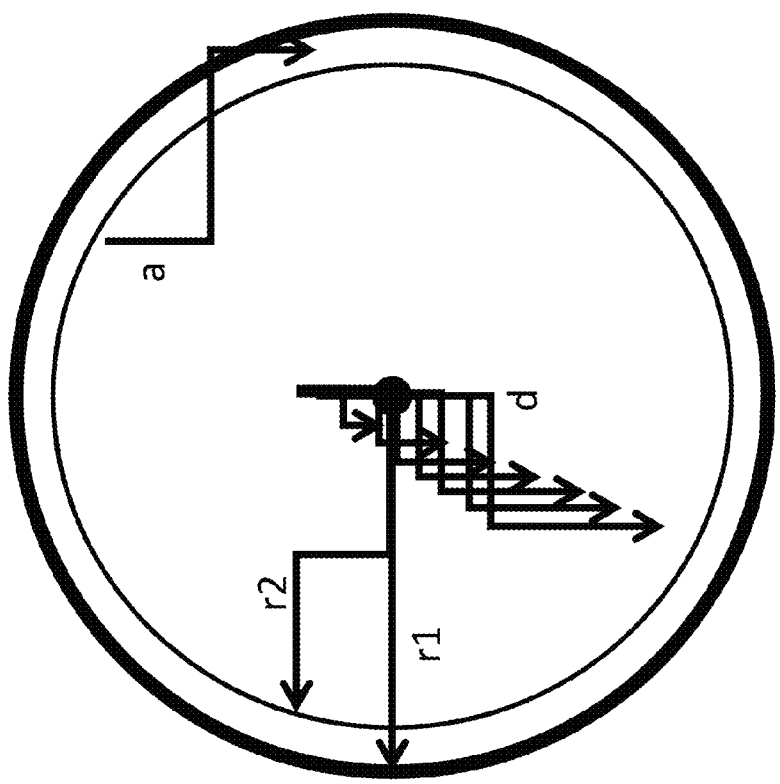

AUTOMATED GENERATION OF GENETICALLY MODIFIED STEM CELLS

CROSS REFERENCE TO RELATED APPLICATIONS

This application claims priority to U.S. Provisional Application No. 61/983,534 filed Apr. 24, 2014 and incorporated by reference herein in its entirety.

STATEMENT REGARDING FEDERALLY SPONSORED RESEARCH

Not applicable.

STATEMENT REGARDING MICROFICHE APPENDIX

Not applicable.

TECHNICAL FIELD

The invention relates to the automated generation of modified cells.

BACKGROUND

Current processes that have been developed for the manufacture of cellular products for cellular therapies, as well as ex vivo genetic manipulation of these cells, have until now been carried out manually or at best by using semi-automated procedures.

For example, cellular therapy of hereditary monogenic genetic disorders, like primary immunodeficiencies, can effectively be treated by overexpression of the wild-type gene product via viral modification of isolated CD34+ progenitor cells (Rivat et al. 2012, Human Gene Therapy 23: 668-675). The generation of this type of cellular product involves the following distinct steps (e.g. Scaramuzza et al. 2013, Mol. Ther 21: 174-184):

(1) Generation of peripheral blood mononuclear cells (PBMC) by Ficoll gradient separation or erythrocyte reduction
(2) Magnetic labeling and magnetic enrichment of the CD34+ cell population
(3) Cultivation and pre-activation of the enriched CD34+ cells with a cytokine cocktail (hTPO, hSCF, hFlt-3L, hIL-3)
(4) Transduction of the pre-activated CD34+ cells with retroviral or lentiviral vectors containing the therapeutic expression cassette
(5) Washing of the final cell product and resuspension in buffer for infusion.

PBMC preparation, magnetic labeling and wash steps are performed manually by centrifugation in tubes and bags. CD34+ cell cultivation, pre-activation and lentiviral transduction are performed in flasks or bags coated with a fibronectin fragment with manual addition of reagents. In current optimized protocols (e.g. Scaramuzza et al. 2013, Mol. Ther.), two transduction cycles with high dose vector are performed.

If cellular therapies and gene therapies are to move from their current translational setting into routine clinical use, a standardized production of cellular therapeutic agents and their genetic modification is required.

Furthermore, genetic modification of stem cells using viral vectors is hampered by the low efficiency of viral transduction and the low numbers of stem cells available for modification from some patient groups (e.g. infants with primary immunodeficiencies). To improve transduction efficiency of stem cells, a method to cultivate the cells at enhanced concentration with a high concentration of viral vector is required (Chuck et al., 1996, Human Gene Therapy; Haas et al., 2000, Mol. Ther.). To prepare stem cells from patient samples, large volumes of blood products and large cell numbers must be processed, requiring a processing chamber with a large volumetric capacity. For genetic modification of small numbers of stem cells, ideally a small cell cultivation chamber would be used to allow cultivation at increased cell density and virus concentration.

Accordingly, it was an object of the invention to provide a process for genetic modification of stem cells starting with a cell sample having a large volume using a centrifugation chamber providing an appropriate processing volume for the cell sample and inducing genetic modification of stem cells suspended in a much smaller volume of liquid with good yield in the same (large volume) centrifugation chamber. Furthermore, the process should enable a closed and highly automated manufacturing procedure.

SUMMARY

Object of the invention is a process for generation of genetically modified stem cells comprising the steps
a) providing a cell sample in suspension comprising stem cells in a centrifugation chamber comprising a base plate and cover plate connected by a cylinder
b) adjusting the volumetric concentration of stem cells in the cell sample to at least $1 \times 10^5$ stem cells per mL cell sample by centrifugation
c) Introducing viral and/or non-viral vectors to the centrifugation chamber for genetically modifying the stem cells
d) adjusting the spatial concentration of stem cells in the centrifugation chamber by rotating the centrifugation chamber at a speed where the cell sample is located at the outermost 35% of the radius of the base plate of the centrifugation chamber, thereby inducing gene modification of the stem cells.

The process is especially suited for gene modifying stem cells like long-term repopulating haematopoeitic stem cells or progenitor cells thereof.

The cell sample may originate from a donor or a patient in the form of a blood product such as whole blood, bone marrow or a sample obtained from leukapheresis. After the process of the invention, the gene modified stem cells can be either administered (directly or formulated) to the patient.

Preferably, the process is performed in a closed and sterile system, for example as disclosed in WO2009/072003. This system and the associated tubing sets are commercially available under the trade name CliniMACS Prodigy® from Miltenyi Biotec GmbH and meet the requirements of GMP-grade processing of almost any kind of cellular product. The system has been developed to fully automate and standardize the manufacturing process of cellular therapeutic agents. The instrument can perform sample loading, cell washing, density-based cell separations including erythrocyte reduction and plasma harvesting, magnetic separation, cell culture, and final product formulation. The CliniMACS Prodigy maintains a closed system by combining single-use disposable tubing sets equipped with multiple input lines with sterile filters or tubing connections for use of sterile docking devices. Output lines offer in-process control if needed.

BRIEF DESCRIPTION OF THE DRAWINGS

Various exemplary details are described with reference to the following figures, wherein:

FIG. 2 shows the areas covered by the cell sample at various rotational speeds;

DETAILED DESCRIPTION

Figure 1A:
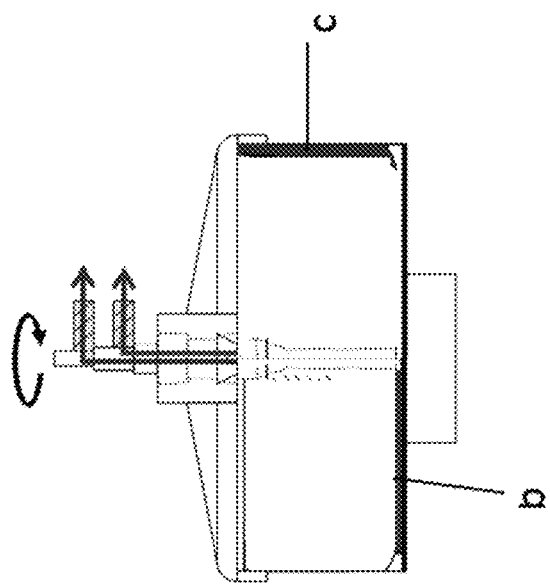
FIG. 1 a, b show a centrifugation chamber and the location of cells at various rotational speeds.

The process of the invention is directed to the genetic modification of stem cells, which are rare cells present in blood and bone marrow and which are only available in rather low amounts. In order to obtain stem cells from patient samples, large volumes of blood products and large cell numbers must be processed, requiring a processing chamber with a large volumetric capacity. On the contrary, for genetic modification of small numbers of stem cells, a small cell cultivation chamber would be used to allow cultivation at increased cell density and virus concentration. The present invention provides a method which enhances the yield of genetically modified target cells in a large chamber by the use of several centrifugation steps.

The procedure prior to steps a-d) of the process may comprise additional gradient separation steps, erythrocyte reduction, platelet removal, cell washing, cell enrichment and/or depletion steps.

Optionally, in a procedure prior to step a) of the process, the cell sample comprising stem cells may be enriched to a higher purity and/or to achieve a first volume reduction. This step can be performed in the same centrifugation chamber and may comprise one or more cell sorting and/or cell washing steps.

In a first embodiment of the invention, prior to step a), the stem cells are labeled by binding an antibody-coupled label to a cell surface marker present on the surface of the stem cell and enriching the labeled stem cells in the cell sample.

In another embodiment of the invention, prior to step a) the cell sample is provided with an antibody-coupled label binding to a cell surface marker not present on the surface of the stem cells and depleting the labeled cells from the cell sample.

The enriching/depleting steps are disclosed in more detail in the further course of this application.

Then, in step b), the concentration of the stem cells is enhanced by reducing the volume of the sample by centrifugation of the cultivation chamber and removal of liquid. This centrifugation step is required to adjust the volumetric concentration of the sample comprising the stem cells to at least $1 \times 10^5$ stem cells per mL cell sample. Preferably, the volumetric concentration of stem cells is increased to at least $1 \times 10^6$ stem cells per mL cell sample, at best to at least $1 \times 10^7$ stem cells per mL cell sample.

This centrifugation step is preferably performed at a rotational speed of the chamber where the cells in the sample are forced to the side wall (the cylinder of the centrifugation chamber), i.e. step b) is performed by rotating the centrifugation chamber providing the cells in the sample with centrifugal forces larger than 4×g, like 5 to 1000×g, preferably 300 to 600×g. At such speed, the supernatant liquid can be removed from the chamber, resulting in a volumetric concentration of the stem cells.

In step c), and optionally after a period of culture, viral vector may be added to the centrifugation chamber and the stem cells are transduced. Step c) may be performed several times with the same or a different transducing agent and/or transducing enhancer, separated by culture periods and/or washing steps. In step c), viral and/or non-viral vectors for genetically modifying the stem cells and optionally transduction enhancers are introduced into the centrifugation chamber, and the cells are genetically modified. For this purpose, the stem cells and the vectors need to be brought as close to each other as possible. It has been found that reducing the spatial and volumetric concentration of the cells greatly enhances the yield of gene modified cells.

Before and/or during step c), the stem cells may optionally be preactivated with one or more cytokines to make them more susceptible to genetic modification with, for example, lentiviral vectors.

The stem cells are gene-modified by the process of the invention. The term "gene-modified" comprises transduction and/or transfection. Preferably, transduction is performed with retroviruses, lentiviruses, gamma and alpharetroviruses or adenoviruses. Transfection may be initiated by nucleic acids (DNA, mRNA, miRNA, antagomirs), proteins, site-specific nucleases (zinc finger nucleases, TALENs, CRISP/R) or integration-deficient lentiviral vectors. The process of the invention may comprise one or more transduction and/or transfection steps. In another embodiment, the process may include an additional gene-modification step of stem cells by electroporation.

Viral transduction of the stem cells may be enhanced by the use of transduction enhancer reagents, especially transduction enhancer reagents selected from the group polycationic reagents (polybrene, protamine sulphate, poly-L-lysine, peptides with a net positive charge, amphipathic cationic peptides), poloxamers, adhesion molecules such as fibronectin or modified fibronectin (RetroNectin), protein targeting domains such as antibodies, antibody complexes, magnetic particles.

The transduction enhancers may be provided in solution, coated on the cultivation chamber or coated on a carrier substance present in suspension/solution within the cultivation chamber.

The centrifugation in step d) leads to the liquid within the chamber collecting at the corners of the cultivation chamber along with the cells and enables the cultivation of cells at high concentration (volumetric concentration: cells per mL and spatial concentration: cells per $cm^2$) in a low volume of liquid. Centrifugation at higher relative g-forces, for example higher than 4 g, may spread the cells over a large area on the side of the cultivation chamber, so reducing the likelihood that viral vector will contact the stem cells.

The spatial concentration of the cells is reduced by adjusting the speed of rotation of the centrifugation chamber in a way that the cell sample is forced to the outermost 10-35%, preferably 10-25% of the radius of the base plate of the centrifugation chamber. FIG. 1a shows the location of cells in a centrifugation chamber at different speeds of rotation. At high speed (for example as used in step b), the cells are located on the whole surface of the cylinder (c) of the chamber. Due to the large surface area, stem cells and vectors are likely to be separated from each other, resulting in low gene modification yields. At low speed or in idle status, the cells are located on the whole surface of the base plate (b) of the chamber. Again, due to the large surface, stem cells and vectors are likely to be separated from each other, resulting in low gene modification yields.

In the process of the invention, the spatial concentration of the cells is preferably adjusted in step d) by rotating the centrifugation chamber providing the stem cells with centrifugal forces of 0.3 to 4.0×g, preferably 0.3 to 1.0×g.

In selecting this rotation speed, the spatial concentration of the cells is optimized and the yield of gene modified cells enhanced.

Figure 1B:
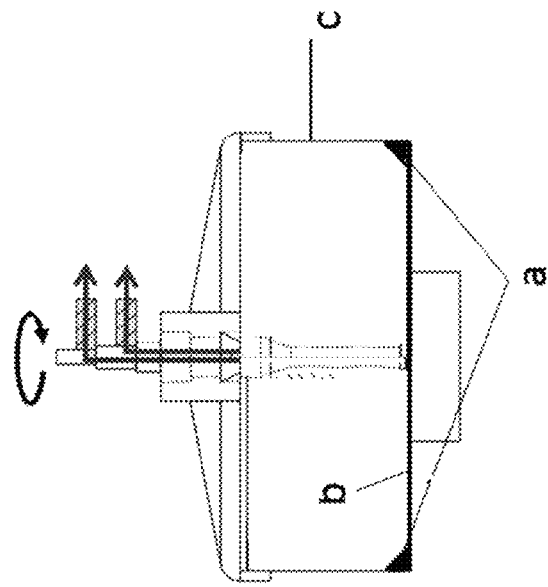

The enhanced spatial concentration of the cells is shown in the following example: In a centrifugation chamber, for example as shown in FIG. 1, having a radius of 6 cm and a height of the cylinder of 4 cm, the surface area of the base plate and the cylinder can be calculated as 113 cm$^2$ and 151 cm$^2$, respectively. By adjusting the speed of rotation of the centrifugation chamber in a way that the cell sample is forced to the outermost 10-25% of the base plate, the radius of the base plate "free from cells" is between 5.4-4.5 cm or calculated as area between 91.6 cm$^2$-63.6 cm$^2$.

FIG. 2 shows by way of example and not in scale, r1 as the radius of the base plate, i.e. $(r1)^2 \times \pi$ defines the area of the base plate covered by the cell sample in idle state of the centrifugation chamber. By rotating the chamber, the cell sample is forced by the centrifugational forces to the outside of the chamber as depicted by the arrows (d), depending on the speed of rotation. r2 stands for the radius to which the cell sample is forced during the process of the invention. The area covered by the cell sample (a) can be calculated by the formula $(r1)^2 \times \pi - (r2)^2 \times \pi$.

In the given example, the area (a) covered by cells is between 21.4 cm$^2$-49.4 cm$^2$ or with respect to the surface area of the base plate the cells are concentrated on 21.4/113=18.9% or 40.6/113=44% of the base plate area. The area where the cells are located is marked in FIGS. 1 and 2 with (a). On the other hand, too high a rotational speed would distribute the cells over the entire surface of the cylinder (i.e. close to 0% of the outermost of the radius of the base plate of the centrifugation chamber), which would lead in this example to an enlargement of the area covered by cells rather than a reduction.

The procedure prior to steps a-d) of the process may comprise additional gradient separation steps, erythrocyte reduction, platelet removal and/or cell washing.

Stem Cells

The process according to the invention is especially suitable for gene manipulation of long-term repopulating haematopoeitic stem cells or progenitor cells thereof. True long-term repopulating haematopoetic stem cells comprise only a small fraction (<0.01%) of the stem cell and progenitor stem cell population characterized by the stem cell marker CD34 (Kim et al. 2014, Cell Stem Cell 14: 473-485). The vast majority of the CD34+ cell population are multi-lineage progenitor cells with short-term engraftment capability as well as cells lacking engraftment capability, which are more differentiated and lineage restricted (McKenzie et al. 2006, Nature Immunol. 2: 75-82). Preferably, the process according to the invention is utilized for gene modification of stem cells which are identified by the expression, coexpression or absence of certain cell surface markers as further described below.

For genetic modification of stem cells with particular characteristics, it is advantageous to modify preferentially the stem cell subpopulations containing these characteristics. These different subpopulations can be identified by flow cytometry by the presence or absence of certain cell surface markers. While CD34 is the classical marker used to define haematopoeitic cells with stem cell characteristics, numerous other markers or combinations of markers can be used to characterize distinct subpopulations with different functional phenotypes. For example, CD133 defines a more restricted population of haematopoeitic stem cells containing the long-term repopulating characteristics. The absence of CD38 or the low expression of this marker also correlates with long-term engraftment capability and the most primitive population (MPP) can be further defined by the absence of CD45RA expression (MPP: CD34+CD133+CD38neg/dim CD45RAneg). Other markers define populations of more differentiated cells already committed to generate cells of certain lineages (e.g. lymphoid primed progenitors (LMPP: CD34+CD133+CD38neg/dim CD45RA+), common myeloid progenitors (CMP: CD34+CD133neg CD38+ CD45RAneg) or granulocyte-macrophage progenitors (GMP: CD34+CD133+CD38neg/dim CD45RA+)).

Cell Enrichment/Depletion

Prior to steps a-d), the stem cells may be enriched utilizing a marker known in the art of cell separation. This can be achieved by either enriching the stem cells or depleting the non-stem cells, i.e. by a cell sorting process.

In a further embodiment of the process of the invention prior to step a), prior to step a), the cell sample is provided with an antibody-coupled label binding to a cell surface marker present on the surface of the stem cells and enriching the labeled stem cells from the cell sample. In other words, the stem cells are labeled by binding an antibody-coupled label to a cell surface marker present on the surface of the stem cell and enriched in the cell sample by sorting the cells for presence of the marker.

In an alternative variant, prior to step a), the cell sample is provided with an antibody-coupled label binding to a cell surface marker not present on the surface of the stem cells and depleting the labeled cells from the cell sample.

Preferably, the stem cells to be genetically modified may be identified by the expression, coexpression or absence of one or more cell surface markers selected from the group consisting of CD34, CD133, CD38, CD45RA, CD49f, CD90, CD150.

The process of the invention may include one or more enrichment and/or depletion steps utilizing the surface markers accordingly. More precise, the cell sorting process may make use of the following combinations of surface markers: CD34+, CD133+, CD34+CD133+, CD34+CD38neg/dim, CD34+CD133+CD38neg/dim CD45RAneg, CD34+CD133+CD38neg/dim CD45RA+, CD34+CD133neg CD38+CD45RAneg, CD34+CD133+CD38neg/dim CD45RA+. In this list, (+) stands for the presence of the respective marker and neg or dim for the absence of the respective marker. For example, cell sorting may only consist of enriching stem cells expressing CD34+ as surface marker or in another process, first depleting cells expressing CD38 and a second enrichment of stem cells expressing CD34+ but lacking CD38 (i.e. neg/dim).

In a first variant of a cell sorting step, the antibody-coupled label is an antibody-coupled magnetic bead and the cells are sorted by a magnetic field.

In a second variant of the sorting step, the antibody-coupled label is an antibody-coupled florescence dye and the cells are sorted by means of detecting the florescence marker. Suitable sorting systems are based on antibody-coupled florescence dye like FACS or flow sorting with microelectromechanical systems (MEMS) technology as disclosed in EP03742110.

For example, the cell sample may first be centrifuged as defined in step b) to adjust stem cell concentration, then washed, magnetically labeled with a magnetic cell separation reagent such as CliniMACS CD34 Reagent (Miltenyi Biotec GmbH), again washed, magnetically enriched via a magnetic cell selection column and then returned to a cell culture chamber. For example, in the system disclosed in WO2009/072003 this embodiment of the invention may be performed by enriching CD34 cells magnetically in a first tubing set such as CliniMACS Prodigy Tubing Set TS310 by Miltenyi Biotec GmbH and the positive fraction containing enriched CD34+ cells is welded off the first tubing set and welded onto a second tubing set CliniMACS Prodigy Tubing Set TS730 by Miltenyi Biotec GmbH for further cultivation, preactivation, transduction and washing.

In the process according to the invention, the stem cells may be enriched by one or several or a combination of positive enrichment (direct magnetic labeling of stem cells) or negative enrichment (direct labeling of non-stem cells) of cells or of the depletion of cellular subsets to be removed from the preparation.

Device/System

Preferably, the process of the invention is performed in a closed and sterile system, comprising a centrifugation chamber comprising a base plate and cover plate connected by a cylinder, pumps, valves, optionally a magnetic cell separation column and a tubing set. The blood samples or purified stem cells are transferred to and from the tubing set by sterile docking or sterile welding. A suitable system is disclosed in WO2009/072003.

A simplified workflow of the process of the invention may have a duration of approximately 3 days and can be outlined as follows:

Tubing set installation and priming
Sample loading, cell washing and volume adjustment
Immunomagnetic labelling and magnetic cell selection
Stem cell cultivation and pre-activation
Genetic modification of enriched stem cells
Stem cell cultivation
Washing and formulation of gene modified stem cells The steps of the stem cell transduction process of the invention may be performed in different closed tubing sets wherein the transfer of the product of one step generated in a first tubing set to a second tubing set can be performed by sterile means.

INDUSTRIAL APPLICABILITY

The process of the invention may be used for the automated generation of modified cells, especially stem cells for cell therapy

EXAMPLES

Comparative Example 1

Automated CD34 Cell Enrichment in CliniMACS Prodigy

Figure 3:
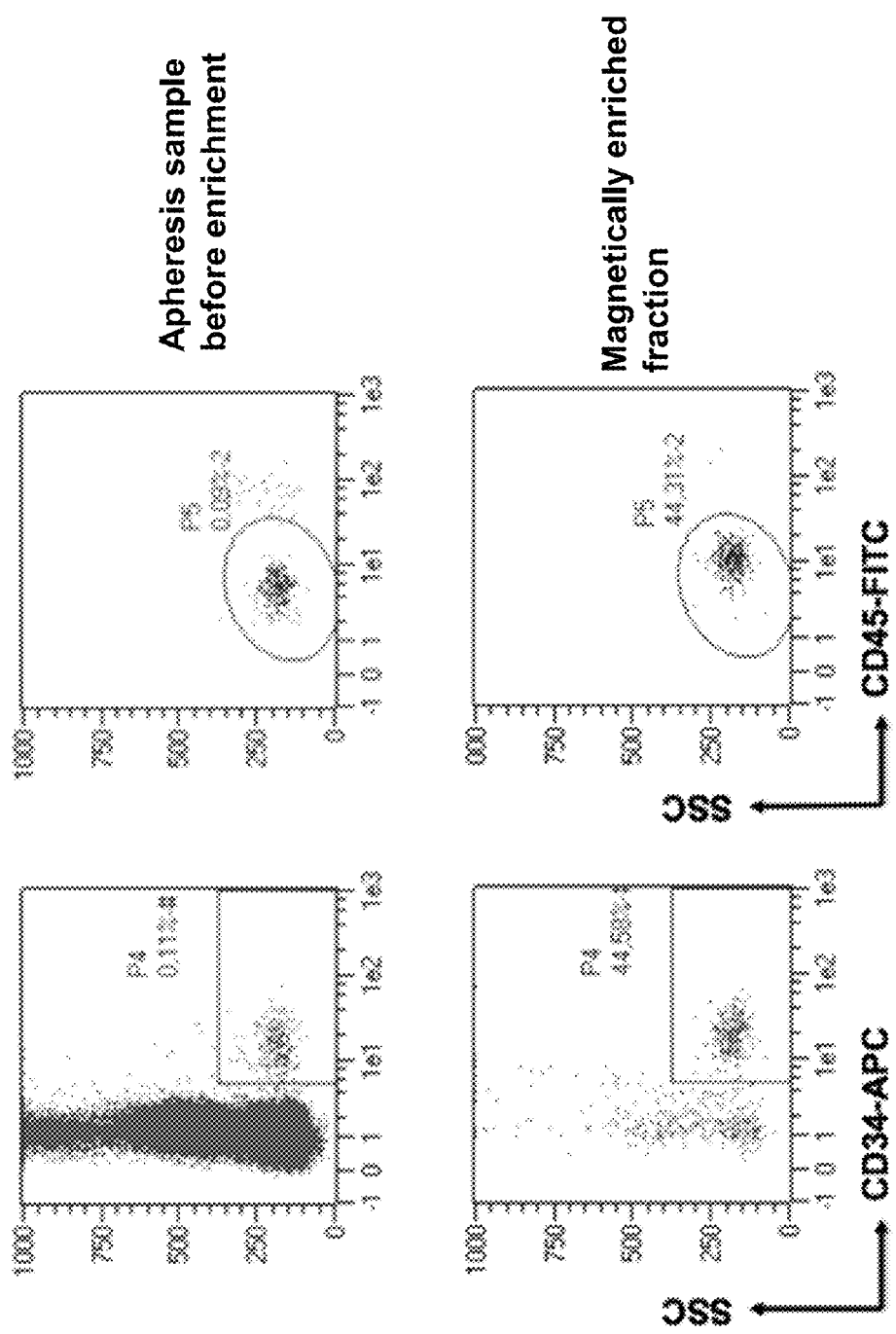
FIG. 3 shows CD34+ cell frequencies in donor samples (upper row) and magnetically enriched fraction (lower row)

Non-mobilised apheresis harvests were processed by labeling stem cells with CliniMACS CD34 Reagent and isolating said CD34+ cells using the CliniMACS Prodigy TS310 tubing set and CliniMACS Prodigy instrument, resulting in cells with purity of 39.3±15.7%, yield of 57.2±12.7% and a depletion of unwanted cells (log-P) of >3.2 (n=16). FIG. 3 shows enrichment data from one of 16 experiments.

Example 1

Cell Density and Viral Vector Concentration are Critical Factors for Efficient Transduction of CD34 Cells Primary CD34+ cells were isolated from a donor apheresis sample using CD34 Reagent and CliniMACS technology. Cells were cultured in CellGro SCGM medium for 24 hours in 24-well plates at $4\times10^5$ cells per mL supplemented with Flt-3L, SCF, IL-3 and TPO. Cell concentration was then adjusted to $10^5$, $10^6$ or $10^7$ per mL and the cells were transduced once or twice with purified lentiviral vector encoding GFP at an MOI=10 or MOI=100. In some duplicate samples, the cell culture dishes were pre-coated with RetroNectin. 24 h post-transduction, the cells cultivated at $10^7$ per mL were diluted to $10^6$ per mL and transduction efficiency was determined at 48 h, 120 h and 14 days post transduction by flow cytometry in a MACSQuant Analyzer.

Figure 4:
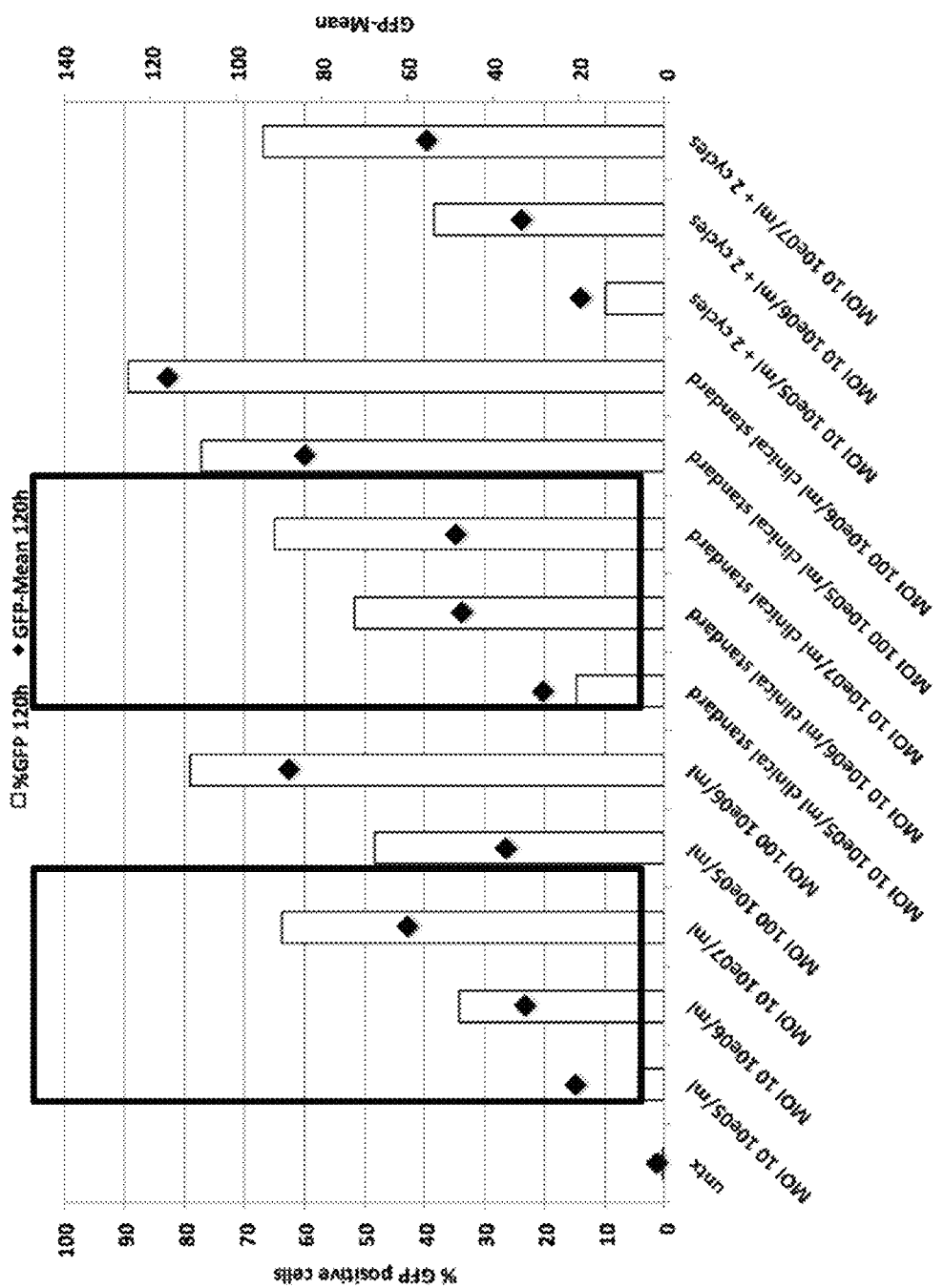
FIG. 4 shows increasing cell and/or vector concentration correlates with increased transduction efficiency of human CD34+ cells.

FIG. 4 shows the gene marking (% GFP positive cells) and GFP fluorescence levels (GFP mean) 120 hours post-transduction. The "clinical standard" samples correspond to 2 cycles of transduction in cell culture dishes pre-coated with RetroNectin. FIG. 4 shows that increasing cell and/or vector concentration clearly correlate with increased transduction efficiency.

Example 2

Low Speed Centrifugation Allows Transduction of Jurkat Target Cells in a Large Cell Culture Vessel (CentriCult Unit) in a Low Volume Jurkat cells express the cell surface marker CD34 and were used as a model CD34+ stem cell system. These cells were cultivated in static conditions in a T75 flask in 20 mL at $1.2\times106$ cells/mL, in a T175 flask or in the Prodigy CentriCult unit in 50 mL at $0.5\times10^6$ cells/mL or while undergoing low speed centrifugation in the Prodigy Centri-Cult unit in 20 mL at $0.9\times10^6$ cells/mL. In this latter example, the cells were first centrifuged at 100 rpm for 10 seconds to collect the cells at the corner of the chamber. Then the cells were cultivated at a relative g-force of 0.4×g. This centrifugation leads to the liquid within the chamber collecting at the corners of the CentriCult unit along with the cells and enables the cultivation of cells at high concentration (volumetric concentration: cells per mL and spatial concentration: cells per $cm^2$) in a low volume of liquid. Centrifugation at higher relative g-forces, for example>4×g, spreads the cells over a large area on the side of the CentriCult unit.

Figure 5:
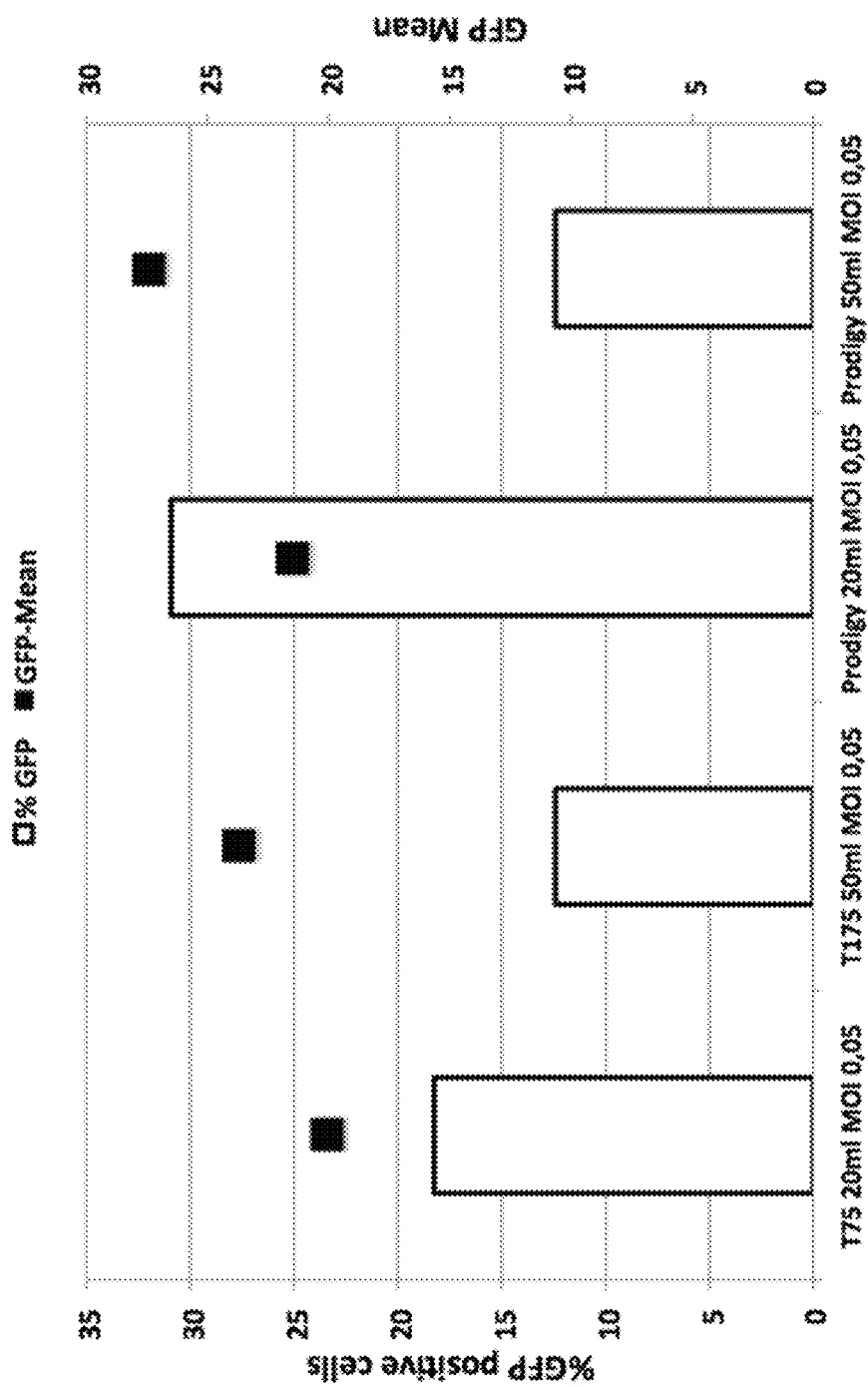
FIG. 5 shows that transduction of Jurkat cells in lower volumes and higher cell densities in flasks or the CentriCult unit results in higher transduction efficiencies.

After one hour, and each hour thereafter, the centrifugation was stopped and the cells centrifuged briefly at 100 rpm in the opposite direction to collect the cells at the edge of the chamber again before continuing the cultivation at 0.4 g in this opposite direction for an hour. These steps were repeated every hour of the cultivation. During the centrifugation, the cells were transduced with a GFP-encoding SIN lentiviral vector at an MOI=0.05 that had been titred on HT1080 cells. FIG. 5 shows that transduction of cells in a lower volume (higher cell and viral vector concentration, $0.9 \times 10^6$ cells/mL compared to $0.5 \times 10^6$ cells/mL) resulted in higher transduction efficiencies (% GFP positive cells) in both static and centrifuged samples.

Example 3

Efficient Transduction of Low Numbers of CD34+ Cells

Figure 6:
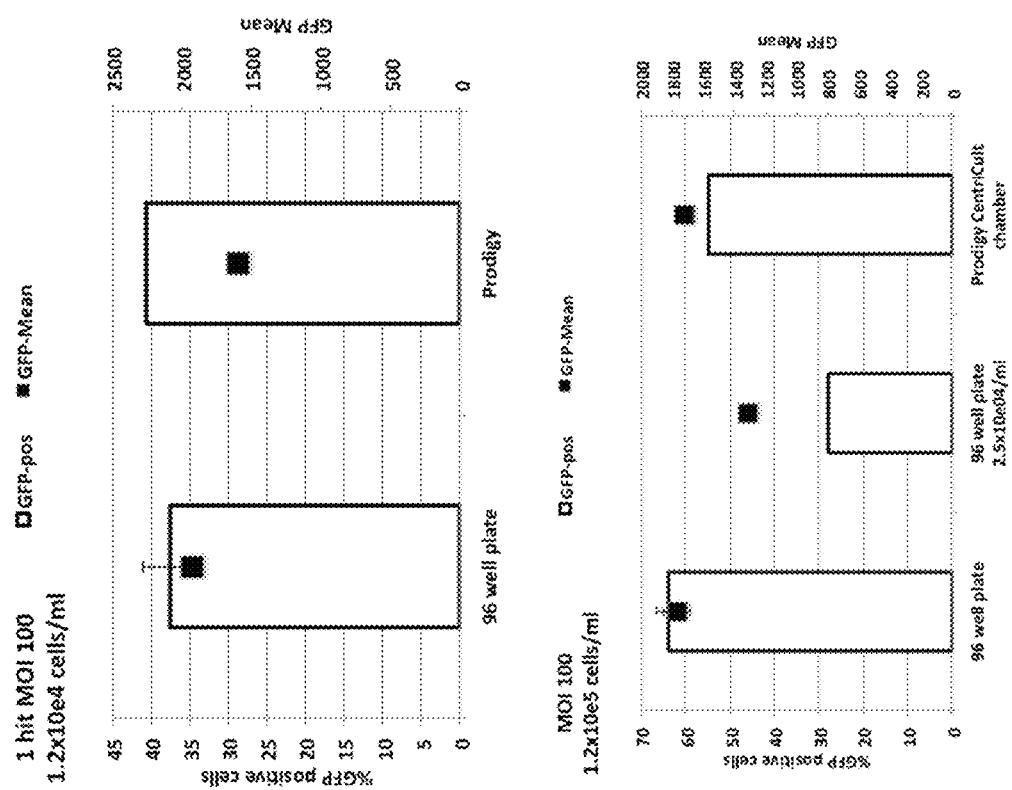
FIG. 6 shows results of the Stem Cell Transduction Process (SCT) with gene modification at $1.25 \times 10^4$ and $1.25 \times 10^5$ cells per ml.
Figure 7:
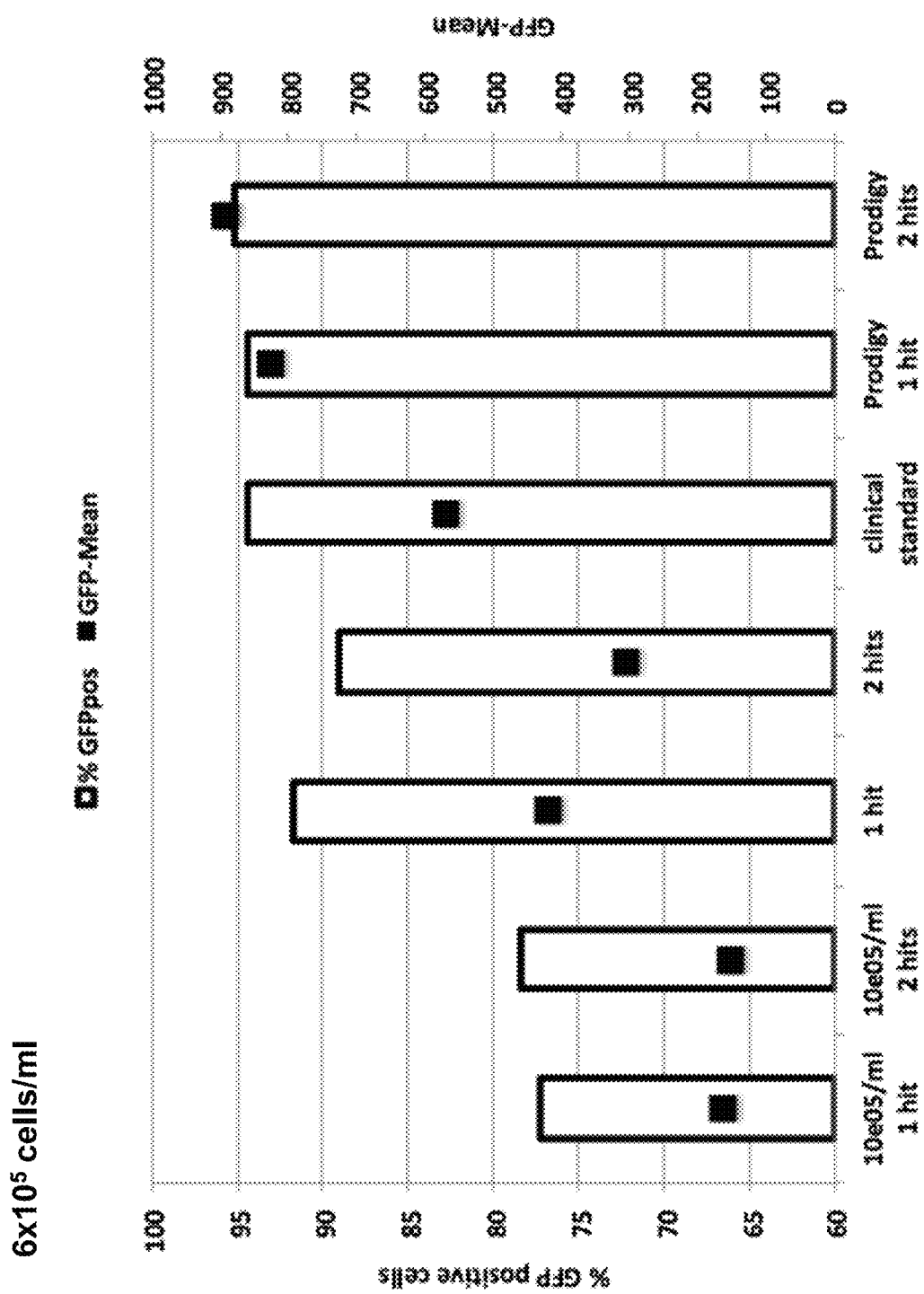
FIG. 7 shows results of the Stem Cell Transduction Process (SCT) with gene modification at $6 \times 10^5$ cells per ml.

CD34+ cells were enriched from bone marrow or apheresis material using the Prodigy device and CD34 Micro-Beads, and were gene modified by transduction in the CentriCult centrifugation chamber (Miltenyi Biotec GmbH) unit under low speed centrifugation as described in Example 2. FIGS. 6 and 7 show that increasing cell and viral vector concentration from $1.25 \times 10^4$ to $1.25 \times 10^5$ to $6 \times 10^5$ cells per mL while maintaining the culture volume at 20 mL enabled more efficient automated transduction of the stem cells. At higher cell concentrations ($6 \times 10^5$ cells per mL) a single "hit" (a single round of transduction) was adequate to reach transduction efficiencies (% GFP) and expression levels (Mean fluorescence intensity, MFI) similar or higher than the standard 2 hit (clinical standard) transduction protocol that additionally uses the transduction enhancer RetroNectin.

The process was performed with the following steps:
CD34+ cells isolated from bone marrow and apheresis samples
Cultivation in CellGro medium supplemented with hTPO, hSCF, hFlt-3L, hIL-3
Transduction with SIN-SFFV-GFP lentiviral vector
1 or optionally 2 hits at an MOI=100
Analysis of genetic modification by flow cytometry using a MACSQuant Analyzer at day 6 (FIG. 6) or 5 (FIG. 7)

Example 4

Figure 8:
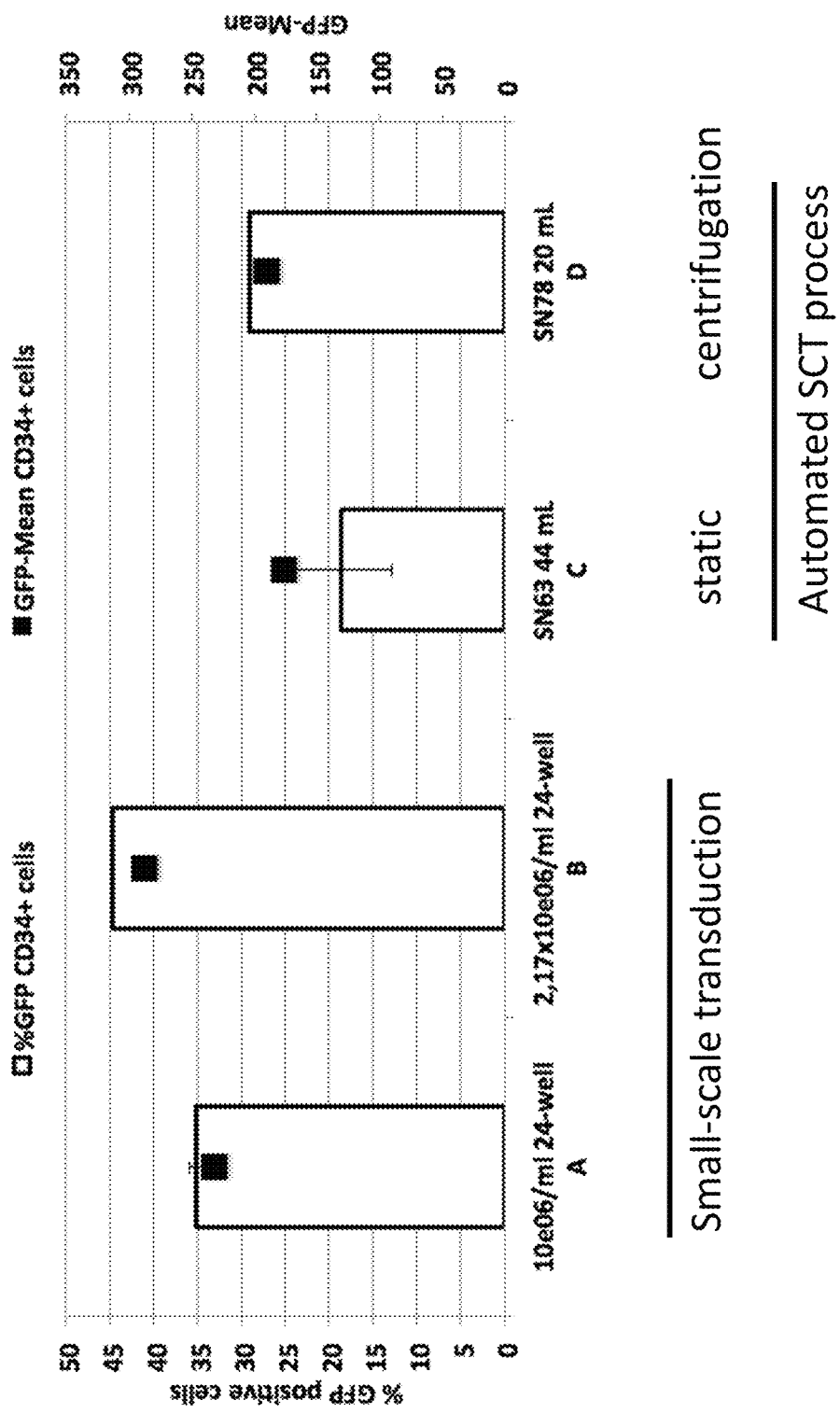
FIG. 8 shows results of the Stem Cell Transduction Process (SCT) with gene modification at $1 \times 10^6$ per ml and $2.17 \times 10^6$ per ml.

Comparative Study Demonstrating Efficient Automated Transduction CD34+ Cells at Higher Cell Density CD34+ cells were enriched from bone marrow or apheresis material using the Prodigy device and CD34 Micro-Beads, and were gene modified by transduction either under static conditions in 24 well plates or in the CentriCult centrifugation chamber of a CliniMACS Prodigy device (Miltenyi Biotec GmbH) under low speed centrifugation as described in Example 2. $1 \times 10^8$ enriched CD34+ cells were preactivated overnight with cytokines at a cell concentration of $2 \times 10^6$ cells per ml in 2 separate CliniMACS Prodigy instruments. The next day, the cell concentration in each instrument was adjusted by centrifugation and fresh medium containing cytokines and a GFP expressing lentiviral vector were added to result in cell densities of $2.17 \times 10^6$ per ml (SN78) and $1 \times 10^6$ per ml (SN63) in a volume of 20 ml or 44 ml respectively. Lentiviral vector was added at an MOI of 20. The cells in instrument SN78 were cultivated under low-speed centrifugation at 0.4×g, the cells in instrument SN68 were cultivated under static conditions. As shown in FIG. 8, the cultivation using the process of the invention (D) at $2.17 \times 10^6$ per ml resulted in a higher transduction efficiency (% GFP positive cells), measured at 13 days post transduction by flow cytometry compared to cells cultivated in a static manner (C) at $1 \times 10^6$ per ml. Stem cells cultivated in a non-automated manner in small cell culture vessels (in 24-well plates) showed a similar trend with cell culture at higher cell densities (B) demonstrating a higher gene modification efficiency than at lower density (A).

FIGS. 5, 6, 7 and 8 show the clinical Stem Cell Transduction Process (SCT) by gene modification according the process of the invention using the closed and sterile system CliniMACS Prodigy.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A process for generation of genetically modified stem cells comprising the steps:
 a) providing a cell sample in suspension comprising stem cells in a centrifugation chamber comprising a base plate and cover plate connected by a cylinder;
 b) adjusting the volumetric concentration of stem cells in the cell sample to at least $1 \times 10^5$ stem cells per mL cell sample by centrifugation;
 c) Introducing viral and/or non-viral vectors to the centrifugation chamber for genetically modifying the stem cells; and
 d) adjusting the spatial concentration of stem cells in the centrifugation chamber by rotating the centrifugation chamber at a speed where the cell sample is located at the outermost 35% of the radius of the base plate of the centrifugation chamber, thereby inducing gene modification of the stem cells.

2. The process according to claim 1, wherein prior to step a), the cell sample is provided with an antibody-coupled label binding to a cell surface marker present on the surface of the stem cells and enriching the labelled stem cells from the cell sample.

3. The process according to claim 1, wherein prior to step a), the cell sample is provided with an antibody-coupled label binding to a cell surface marker not present on the surface of the stem cells and depleting the labelled cells from the cell sample.

4. The process according to claim 2, wherein the antibody-coupled label is an antibody-coupled magnetic bead and the cells are sorted by a magnetic field.

5. The process according to claim 2, wherein the antibody-coupled label is an antibody-coupled florescence dye and the cells are sorted by a means detecting the florescence marker.

6. The process according to claim 2, wherein the cell surface marker is selected from the group consisting of CD34, CD133, CD38, CD45RA, CD49f, CD90, and CD150.

7. The process according to any of the claim 1, wherein step d) is performed by rotating the centrifugation chamber providing the stem cells with centrifugal forces of 0.3 to less than 4.0×g.

8. The process according to claim 1, wherein step b) is performed by rotating the centrifugation chamber providing the cells in the sample with centrifugal forces of 4.0 to 400.0×g.

9. The process according to claim 1, wherein the viral vector in step c) is a retrovirus, lentivirus, gamma, alpharetrovirus and/or adenovirus.

10. The process according to any of the claim 1, wherein gene modification of the stem cells is performed in the presence of transduction enhancers.

11. The process according to claim 10, wherein the transduction enhancers are selected from the group consisting of polybrene, protamine sulphate, poly-L-lysine, peptides with a net positive charge, amphipathic cationic peptides, poloxamers, fibronectin, modified fibronectin, protein targeting domains, antibody complexes and magnetic particles.

12. The process according to claim 1, wherein prior to gene modification of the stem cells, the stem cells are preactivated with one or more cytokines.

13. The process according to claim 1, wherein the stem cells are long-term repopulating haematopoeitic stem cells or progenitor cells thereof.

\* \* \* \* \*